US005525487A

United States Patent [19]

Gallatin et al.

[11] Patent Number: 5,525,487

[45] Date of Patent: Jun. 11, 1996

[54] DNA ENCODING I-CAM RELATED PROTEIN

[75] Inventors: W. Michael Gallatin, Mercer Island; Rosemay Vazeux, Seattle, both of Wash.

[73] Assignee: ICOS Corporation, Bothell, Wash.

[21] Appl. No.: 314,615

[22] Filed: Sep. 28, 1994

Related U.S. Application Data

[63] Continuation of Ser. No. 827,689, Jan. 27, 1992, abandoned.

[51] Int. Cl.[6] .............................. C12P 21/06; C12N 5/10; C12N 15/63; C07K 14/725

[52] U.S. Cl. .................... 435/69.1; 435/69.7; 435/240.1; 435/320.1; 536/23.5; 536/24.31; 530/350

[58] Field of Search ................................ 536/23.1, 23.4, 536/24.31; 435/69.1, 69.3, 69.7, 240.1, 520.1

[56] References Cited

FOREIGN PATENT DOCUMENTS

| | | |
|---|---|---|
| 289949 | 11/1988 | European Pat. Off. . |
| 314317 | 5/1989 | European Pat. Off. . |
| 314863 | 5/1989 | European Pat. Off. . |
| 362531 | 4/1990 | European Pat. Off. . |
| 386906 | 9/1990 | European Pat. Off. . |
| 387668 | 9/1990 | European Pat. Off. . |
| 408859 | 1/1991 | European Pat. Off. . |
| 468257 | 1/1992 | European Pat. Off. . |
| WO88/06592 | 9/1988 | WIPO . |
| WO89/02922 | 4/1989 | WIPO . |
| WO90/05539 | 5/1990 | WIPO . |
| WO90/05786 | 5/1990 | WIPO . |
| WO90/06953 | 6/1990 | WIPO . |
| WO90/13300 | 11/1990 | WIPO . |
| WO91/10683 | 7/1991 | WIPO . |
| WO91/16928 | 11/1991 | WIPO . |
| WO91/18010 | 11/1991 | WIPO . |
| WO91/18011 | 11/1991 | WIPO . |
| WO92/00751 | 1/1992 | WIPO . |
| WO92/04034 | 3/1992 | WIPO . |
| WO92/06119 | 4/1992 | WIPO . |
| WO92/22323 | 12/1992 | WIPO . |

OTHER PUBLICATIONS

Stauton et al 1989 Nature 339:61–64.

Sambrook et al. 1989 Molecular Cloning A Laboratory Manual Cold Spring Harbor Laboratory Press, CSH, NY p. 16.3.

Seed et al 1987 PNAS 84:3365–3369.

Stockinger et al 1990 J. Immunol 145:3889–3897.

Rothlein et al 1986 J. Immunol. 137:1270–1274.

Ashkenazi et al., *Proc. Natl. Acad. Sci. USA*, 88:10535–10539 (1991).

Capon et al., *Nature*, 337:525–531 (1989).

Corpet et al., *Nucleic Acids Res.*, 16(22):10881–10890 (1988).

de Fougerolles et al., *J. Exp. Med.*, 174:253–267(1991).

de Fougerolles et al., *J. Exp. Med.*, 175:185–190 (1992).

Edwards, *Current Opinion in Therapeutic Patents*, 1(11):1617–1630 (1991).

Fawcett et al., *Nature*, 360:481–484 (1992).

Hunkapiller et al., *Nature*, 323:15–16 (1986).

Newman et al., *Science*, 247:1219–1222 (1990).

Springer, *Nature*, 346:425–434 (1990).

Vazeux et al., *Nature*, 360:485–488 (1992).

Williams et al., *Ann. Rev. Immunol.*, 6:381–405 (1988).

Hadam, "N11 Cluster Report: CDw50", pp. 667–670 in Knapp et al., eds., *Leukocyte Typing IV*, Oxford, Oxford University Press (1989).

Juan et al., "CDw50 and ICAM-3: Two names for the same molecule", *Eur. J. Immunol.*, 23:1508–1512 (1993).

Knapp et al., "CD Antigens 1989", *Blood*, 74(4):1448–1450 (Sep. 1989).

Lozano et al., "Effect of protein kinase C activators on the phosphorylation and the surface expression of the CDw50 leukocyte antigen", *Eur. J. Biochem.*, 203:321–326 (Mar. 1992).

Lozano et al., "Isolation and Characterisation of a CDw50 Negative Jurkat T-Cell Line Variant", *Leukemia Research*, 17(1):9–16 (1993).

Vilella et al., "Involvement of the CDw50 molecule in allorecognition", *Tissue Antigens*, 36:203–210 (1990).

DeFougerolles et al., "Cloning and Expression of Intercellular Adhesion Molecule 3 Reveals Strong Homology to the Other Immunoglobulin Family Counter-receptors for Lymphocyte Function-associated Antigen 1", *J. Exp. Med.*, 177:1187–1192 (Apr. 1993).

*Primary Examiner*—Robert A. Wax
*Assistant Examiner*—K. Cochrane Carlson
*Attorney, Agent, or Firm*—Marshall, O'Toole, Gerstein, Murray & Borun

[57] ABSTRACT

DNA sequences encoding a novel human intercellular adhesion molecule polypeptide (designated "ICAM-R") and variants thereof are disclosed along with methods and materials for production of the same by recombinant procedures. Antibodies substances specific for ICAM-R and variants thereof are also disclosed as useful in both the isolation of ICAM-R from natural cellular sources and the inhibition of ligand/receptor binding reactions involving ICAM-R.

25 Claims, 7 Drawing Sheets

```
CAGCTCTCTGTCAGA ATG GCC ACC ATG GTA CCA TCC GTG TTG TGG CCC     48
                M   A   T   M   V   P   S   V   L   W   P
                -29         -26 -25                 -20

AGG GCC TGC TGG ACT CTG CTG GTC TGC TGT CTG CTG ACC CCA GGT     93
R   A   C   W   T   L   L   V   C   C   L   L   T   P   G
            -15                 -10                 -5

GTC CAG GGG CAG GAG TTC CTT TTG CGG GTG GAG CCC CAG AAC CCT     138
V   Q   G   Q   E   F   L   L   R   V   E   P   Q   N   P
        -1  +1              5                   10

GTG CTC TCT GCT GGA GGG TCC CTG TTT GTG AAC TGC AGT ACT GAT     183
V   L   S   A   G   G   S   L   F   V   N*  C   S   T   D
        15                  20                  25

TGT CCC AGC TCT GAG AAA ATC GCC TTG GAG ACG TCC CTA TCA AAG     228
C   P   S   S   E   K   I   A   L   E   T   S   L   S   K
        30                  35                  40

GAG CTG GTG GCC AGT GGC ATG GGC TGG GCA GCC TTC AAT CTC AGC     273
E   L   V   A   S   G   M   G   W   A   A   F   N*  L   S
        45                  50                  55
```

FIGURE 1A

```
AAC GTG ACT GGC AAC AGT CGG ATC CTC TGC TCA GTG TAC TGC AAT     318
N*  V   T   G   N   S   R   I   L   C   S   V   Y   C   N*
        60                  65                  70

GGC TCC CAG ATA ACA GGC TCC TCT AAC ATC ACC GTG TAC GGG CTC     363
G   S   Q   I   T   G   S   S   N*  I   T   V   Y   G   L
        75                  80                  85

CCG GAG CGT GTG GAG CTG GCA CCC CTG CCT CCT TGG CAG CCG GTG     408
P   E   R   V   E   L   A   P   L   P   P   W   Q   P   V
        90                  95                  100

GGC CAG AAC TTC ACC CTG CGC TGC CAA GTG GAG GGT GGG TCG CCC     453
G   Q   N*  F   T   L   R   C   Q   V   E   G   G   S   P
        105                 110                 115

CGG ACC AGC CTC ACG GTG GTG CTG CTT CGC TGG GAG GAG GAG CTG     498
R   T   S   L   T   V   V   L   L   R   W   E   E   E   L
        120                 125                 130

AGC CGG CAG CCC GCA GTG GAG GAG CCA GCG GAG GTC ACT GCC ACT     543
S   R   Q   P   A   V   E   E   P   A   E   V   T   A   T
        135                 140                 145
```

FIGURE 1B

```
GTG CTG GCC AGC AGA GAC GAC CAC GGA GCC CCT TTC TCA TGC CGC    588
 V   L   A   S   R   D   D   H   G   A   P   F   S   C   R
        150                 155                 160

ACA GAA CTG GAC ATG CAG CCC CAG GGG CTG GGA CTG TTC GTG AAC    633
 T   E   L   D   M   Q   P   Q   G   L   G   L   F   V   N*
        165                 170                 175

ACC TCA GCC CCC CGC CAG CTC CGA ACC TTT GTC CTG CCC GTG ACC    678
 T   S   A   P   R   Q   L   R   T   F   V   L   P   V   T
        180                 185                 190

CCC CCG CGC CTC GTG GCC CCC CGG TTC TTG GAG GTG GAA ACG TCG    723
 P   P   R   L   V   A   P   R   F   L   E   V   E   T   S
        195                 200                 205

TGG CCG GTG GAC TGC ACC CTA GAC GGG CTT TTT CCA GCC TCA GAG    768
 W   P   V   D   C   T   L   D   G   L   F   P   A   S   E
        210                 215                 220

GCC CAG GTC TAC CTG GCG CTG GGG GAC CAG ATG CTG AAT GCG ACA    813
 A   Q   V   Y   L   A   L   G   D   Q   M   L   N*  A   T
        225                 230                 235
```

FIGURE 1C

```
GTC ATG AAC CAC GGG GAC ACG CTA ACG GCC ACA GCC ACA GCC ACG   858
 V   M   N   H   G   D   T   L   T   A   T   A   T   A   T
        240                 245                 250

GCG CGC GCG GAT CAG GAG GGT GCC CGG GAG ATC GTC TGC AAC GTG   903
 A   R   A   D   Q   E   G   A   R   E   I   V   C   N*  V
        255                 260                 265

ACC CTA GGG GGC GAG AGA CGG GAG GCC CGG GAG AAC TTG ACG GTC   948
 T   L   G   G   E   R   R   E   A   R   E   N*  L   T   V
        270                 275                 280

TTT AGC TTC CTA GGA CCC ATT GTG AAC CTC AGC GAG CCC ACC GCC   993
 F   S   F   L   G   P   I   V   N*  L   S   E   P   T   A
        285                 290                 295

CAT GAG GGG TCC ACA GTG ACC GTG AGT TGC ATG GCT GGG GCT CGA   1038
 H   E   G   S   T   V   T   V   S   C   M   A   G   A   R
        300                 305                 310

GTC CAG GTC ACG CTG GAC GGA GTT CCG GCC GCG GCC CCG GGG CAG   1083
 V   Q   V   T   L   D   G   V   P   A   A   A   P   G   Q
        315                 320                 325
```

FIGURE 1D

```
CCA GCT CAA CTT CAG CTA AAT GCT ACC GAG AGT GAC GAC GGA CGC    1128
P   A   Q   L   Q   L   N*  A   T   E   S   D   D   G   R
        330                 335                 340

AGC TTC TTC TGC AGT GCC ACT CTC GAG GTG GAC GGC GAG TTC TTG    1173
S   F   F   C   S   A   T   L   E   V   D   G   E   F   L
        345                 350                 355

CAC AGG AAC AGT AGC GTC CAG CTG CGA GTC CTG TAT GGT CCC AAA    1218
H   R   N*  S   S   V   Q   L   R   V   L   Y   G   P   K
        360                 365                 370

ATT GAC CGA GCC ACA TGC CCC CAG CAC TTG AAA TGG AAA GAT AAA    1263
I   D   R   A   T   C   P   Q   H   L   K   W   K   D   K
        375                 380                 385

ACG AGA CAC GTC CTG CAG TGC CAA GCC AGG GGC AAC CCG TAC CCC    1308
T   R   H   V   L   Q   C   Q   A   R   G   N   P   Y   P
        390                 395                 400

GAG CTG CGG TGT TTG AAG GAA GGC TCC AGC CGG GAG GTG CCG GTG    1353
E   L   R   C   L   K   E   G   S   S   R   E   V   P   V

        405                 410                 415
```

FIGURE 1E

```
GGG ATC CCG TTC TTC GTC AAC GTA ACA CAT AAT GGT ACT TAT CAG     1398
G   I   P   F   F   V   N*  V   T   H   N*  G   T   Y   Q
        420                 425                 430

TGC CAA GCG TCC AGC TCA CGA GGC AAA TAC ACC CTG GTC GTG GTG     1443
C   Q   A   S   S   S   R   G   K   Y   T   L   V   V   V
        435                 440                 445

ATG GAC ATT GAG GCT GGG AGC TCC CAC TTT GTC CCC GTC TTC GTG     1488
M   D   I   E   A   G   S   S   H   F---V---P---V---F---V--
        450                 455                 460

GCG GTG TTA CTG ACC CTG GGC GTG GTG ACT ATC GTA CTG GCC TTA     1533
A---V---L---L---T---L---G---V---V---T---I---V---L---A---L--
        465                 470                 475

ATG TAC GTC TTC AGG GAG CAC CAA CGG AGC GGC AGT TAC CAT GTT     1578
M---Y---V---F   R   E   H   Q   R   S   G   S   Y   H   V
        480                 485                 490

AGG GAG GAG AGC ACC TAT CTG CCC CTC ACG TCT ATG CAG CCG ACA     1623
R   E   E   S   T   Y   L   P   L   T   S   M   Q   P   T
        495                 500                 505
```

FIGURE 1F

```
GAA GCA ATG GGG GAA GAA CCG TCC AGA GCT GAG TGACGCTGGGATCCG      1671
E   A   M   G   E   E   P   S   R   A   E
        510                 515         518

GGATCAAAGTTGGCGGGGGCTTGGCTGTGCCCTCAGATTCCGCACCAATAAAGCCTTCA      1730

AACTCCCAAAAAAAAAAAAAAAAAAAAAAAAAAAAAAAAAAAAAAAAAAAA              1781
```

FIGURE 1G

DNA ENCODING I-CAM RELATED PROTEIN

This is a Rule 62 file wrapper continuation of U.S. patent application Ser. No. 07/827,689, filed Jan. 27, 1992, now abandoned.

BACKGROUND OF THE INVENTION

The present invention relates generally to cellular adhesion molecules and more particularly to the cloning and expression of DNA encoding a heretofore unknown human polypeptide designated "ICAM-R" which possesses structural relatedness to the human intercellular adhesion molecules ICAM-1 and ICAM-2.

Research spanning the last decade has significantly elucidated the molecular events attending cell-cell interactions in the body, especially those events involved in the movement and activation of cells in the immune system. See generally, Springer, *Nature,* 346:425–434 (1990). Cell surface proteins, and especially the so-called Cellular Adhesion Molecules ("CAMs") have correspondingly been the subject of pharmaceutical research and development having as its goal intervening in the processes of leukocyte extravasation to sites of inflammation and leukocyte movement to distinct target tissues. The isolation and characterization of cellular adhesion molecules, the cloning and expression of DNA sequences encoding such molecules, and the development of therapeutic and diagnostic agents relevant to inflammatory processes, viral infection and cancer metastasis have also been the subject of numerous U.S. and foreign applications for Letters Patent. See Edwards, *Current Opinion in Therapeutic Patents,* 1(11):1617–1630 (1991) and particularly the published "patent literature references" cited therein.

Of fundamental interest to the background of the present invention is the prior identification and characterization of certain mediators of cell adhesion events, the "leukointegrins," LFA-1, MAC-1 and gp 150.95 (referred to in WHO nomenclature as CD18/CD11a, CD18/CD11b, and CD18/CD11c, respectively) which form a subfamily of heterodimeric "integrin" cell surface proteins present on B lymphocytes, T lymphocytes monocytes and granulocytes. See, e.g., Table 1 of Springer, Supra, at page 429. Also of interest are other single chain adhesion molecules (CAMs) which have been implicated in leukocyte activation, adhesion, motility and the like, events attendant the inflammatory process. For example, it is presently believed that prior to the leukocyte extravasation which characterizes inflammatory processes, activation of integrins constitutively expressed on leukocytes occurs and there follows a tight ligand/receptor interaction between the integrins (e.g., LFA-1) and one or both distinct intracellular adhesion molecules (ICAMs) designated ICAM-1 and ICAM-2, which are expressed on blood vessel endothelial cell surfaces and on other leukocytes.

Like the other CAMs characterized to date, [e.g., vascular adhesion molecule (VCAM-1) as described in PCT WO 90/13300 published Nov. 15, 1990; and platelet endothelial cell adhesion molecule (PECAM-1) as described in Newman et al. *Science* 247:1219–1222 (1990) and PCT WO 91/10683 published Jul. 25, 1991], ICAM-1 and ICAM-2 share structural homology with other members of the immunoglobulin gene superfamily in that each is comprised of a series of domains sharing a similar motif near their ends. An individual domain typically contains a loop structure usually anchored by a disulfide bond between two cysteines at the extremity of each loop. ICAM-1 includes five immunoglobulin-like domains; ICAM-2, which differs from ICAM-1 in terms of cell distribution, includes two such domains; PECAM-1 includes six; VCAM includes six or seven, depending on splice variations, and so on. Moreover, CAMs typically include a hydrophobic "transmembrane" region believed to participate in orientation of the molecule at the cell surface and a carboxy terminal "cytoplasmic" region. Graphic models of the operative disposition of CAMs generally show the molecule anchored in the cell membrane at the transmembrane region with the cytoplasmic "tail" extending into the cell cytoplasm and one or more immunoglobulin-like loops extending outward from the cell surface.

Despite the fundamental insights into cell adhesion phenomena which have been gained by the identification and characterization of intercellular adhesion proteins such as ICAM-1 and lymphocyte interactive integrins such as LFA-1, the picture is far from complete. It is generally believed that numerous other proteins are involved in inflammatory processes and in targeted lymphocyte movement throughout the body. Quite recently, for example, Springer and his co-workers postulated the existence of a third counter-receptor for LFA-1 [de Fougerolles, et al., *J. Exp. Med.,* 174:253–267 (1991)] and subsequently reported success in immunoprecipitating a "third" ICAM ligand, designated "ICAM-3"[de Fougerolles, et al., *J. Exp. Med.,* 175:185–190 (1992)]. This molecule was reported to bind soluble LFA-1 and to be highly expressed by resting lymphocytes, monocytes and neutrophils. Unlike ICAM-1 and ICAM-2, however, the new ligand was not found to be expressed by endothelial cells. The immunoprecipitated product was noted to display a molecular weight of about 124,000 and to be heavily glycosylated, as revealed by a drop in apparent molecular weight to about 87,000 upon N-glyanase treatment.

There thus continues to be a need in the art for the discovery of additional proteins participating in human cell-cell interactions and especially a need for information serving to specifically identify and characterize such proteins in terms of their amino acid sequence. Moreover, to the extent that such molecules might form the basis for the development of therapeutic and diagnostic agents, it is essential that the DNA encoding them be elucidated. Such seminal information would inter alia, provide for the large scale production of the proteins, allow for the identification of cells naturally producing them, and permit the preparation of antibody substances or other novel binding proteins specifically reactive therewith and/or inhibitory of ligand/receptor binding reactions in which they are involved.

BRIEF SUMMARY

In one of its aspects, the present invention provides purified and isolated polynucleotides (e.g., DNA sequences and RNA transcripts thereof) encoding a novel human polypeptide, "ICAM-R," as well as polypeptide variants (including fragments) thereof which display one or more ligand/receptor binding biological activities and/or immunological properties specific to ICAM-R. Preferred DNA sequences of the invention include genomic and cDNA sequences as well as wholly or partially chemically synthesized DNA sequences and biological replicas thereof. Also provided are autonomously replicating recombinant constructions such as plasmid and viral DNA vectors incorporating such sequences and especially vectors wherein DNA encoding ICAM-R or an ICAM-R variant is operatively linked to an endogenous or exogenous expression control DNA sequence.

According to another aspect of the invention, host cells, especially unicellular host cells such as procaryotic and eucaryotic cells, are stably transformed with DNA sequences of the invention in a manner allowing the desired polypeptides to be expressed therein. Host cells expressing such ICAM-R and ICAM-R variant products can serve a variety of useful purposes. To the extent that the expressed products are "displayed" on host cell surfaces, the cells may constitute a valuable immunogen for the development of antibody substances specifically immunoreactive with ICAM-R and ICAM-R variants. Host cells of the invention are conspicuously useful in methods for the large scale production of ICAM-R and ICAM-R variants wherein the cells are grown in a suitable culture medium and the desired polypeptide products are isolated from the cells or from the medium in which the cells are grown.

Novel ICAM-R and ICAM-R variant products of the invention may be obtained as isolates from natural cell sources, but are preferably produced by recombinant procedures involving host cells of the invention. The products may be obtained in fully or partially glycosylated, partially or wholly de-glycosylated, or non-glycosylated forms, depending on the host cell selected for recombinant production and/or post-isolation processing.

Products of the invention include polypeptides having the sequence of amino acid residues numbered −29 through 518 as set out in SEQ ID NO: 1 herein. As explained in detail infra, this sequence includes a putative signal or leader sequence which precedes the "mature" protein sequence and spans residues −29 through −1, followed by the putative mature protein including, in order, five putative immunoglobulin-like domains (respectively spanning residues 1 to 90, 91 to 187, 188 to 285, 286 to 387, and 388 to about 456), a hydrophobic "transmembrane" region extending from about residue 457 to about residue 481 and a "cytoplasmic" region constituting the balance of the polypeptide at its carboxy terminus. Based on amino acid composition, the calculated molecular weight of the mature protein lacking glycosylation or other post-translational modification is approximately 52,417. ICAM-R variants of the invention may comprise ICAM-R fragments including one or more of the regions specified above and may also comprise polypeptide analogs wherein one or more of the specified amino acids is deleted or replaced: (1) without loss, and preferably with enhancement, of one or more biological activities or immunological characteristics specific for ICAM-R; or (2) with specific disablement of a particular ligand/receptor binding function.

Also comprehended by the present invention are antibody substances (e.g., monoclonal and polyclonal antibodies, single chain and chimeric antibodies and the like) or other binding proteins which are specific for ICAM-R or ICAM-R variants (i.e., non-reactive with the ICAM-1 and ICAM-2 intercellular adhesion molecules to which ICAM-R is structurally related). Antibody substances can be developed using isolated natural or recombinant ICAM-R or ICAM-R variants or cells expressing such products on their surfaces. The antibody substances are useful, in turn, for purifying polypeptides of the invention as well as for identifying cells producing the polypeptides on their surfaces. The antibody substances are also manifestly useful in blocking or inhibiting ligand/receptor binding reactions involving ICAM-R and in assays for the detection and quantification of ICAM-R in fluids such as serum.

The scientific value of the information contributed through the disclosures of DNA and amino acid sequences of the present invention is manifest. As one series of examples, knowledge of the sequence of a cDNA for ICAM-R makes possible the isolation by DNA/DNA hybridization of genomic DNA sequences encoding ICAM-R and specifying ICAM-R expression control regulatory sequences such as promoters, operators and the like. DNA/DNA hybridization procedures carried out with DNA sequences of the invention and under stringent conditions are likewise expected to allow the isolation of DNAs encoding allelic variants of ICAM-R, other structurally related proteins sharing the biological and/or immunological specificity of ICAM-R, and non-human species proteins homologous to ICAM-R. Also made available by the invention are anti-sense polynucleotides relevant to regulating expression of ICAM-R by those cells which ordinarily express the same. As another series of examples, knowledge of the DNA and amino acid sequences of ICAM-R make possible the generation by recombinant means of hybrid fusion proteins (sometimes referred to as "immunoadhesins") characterized by the presence of ICAM-R protein sequences and immunoglobulin heavy chain constant regions and/or hinge regions. See, Capon, et at., *Nature*, 337:525–531 (1989); Ashkenazi, et al., *P.N.A.S.* (USA), 88:10535–10539 (1991); and PCT WO 89/02922, published Apr. 6, 1989.

Numerous other aspects and advantages of the present invention will therefore be apparent upon consideration of the following detailed description thereof, reference being made to the drawing wherein FIG. 1(A through G) depicts an isolated cDNA clone insert (SEQ ID NO: 2) derived from HL60 cells encoding ICAM-R and the deduced amino acid sequence (SEQ ID NO: 1) of an open reading frame therein.

BRIEF DESCRIPTION OF THE DRAWINGS

FIGS. 1A–1G depict the amino acid sequence (SEQ. ID NO 1) describing ICAM-R with its putative signal sequence and its encoding nucleic acid sequence (SEQ. ID 2).

DETAILED DESCRIPTION

The present invention is illustrated by the following examples relating to the isolation of a full length cDNA clone encoding ICAM-R from a cDNA library derived from human HL60 promyelocytic cells (ATCC CCL 240) and to the attempted expression thereof in COS-7 and L-cells. More particularly, Example 1 addresses the design and construction of oligonucleotide probes for PCR amplification of ICAM related DNAs. Example 2 addresses the use of the probes to amplify a genomic DNA fragment homologous to, but distinct from, DNAs encoding ICAM-1 and ICAM-2. Example 3 treats the screening of cDNA libraries with the genomic fragment to isolate additional ICAM-R coding sequences. Example 4 refers to the further screening of cDNA libraries to isolate a full length cDNA encoding ICAM-R. Example 5 provides a characterization of DNA and amino acid sequence information for ICAM-R and relates the structures thereof to ICAM-1 and ICAM-2. Example 6 describes the development of host cells expressing ICAM-R.

EXAMPLE 1

Nucleic acid and amino acid alignments of individual sets of CAMs (e.g., ICAM-1 and ICAM-2) did not manifest sufficient conservation between molecules to yield information useful in the design of consensus-type probes for isolating related novel genes. The strategic focus of attempts to isolate unknown DNAs encoding cellular adhesion molecules therefore involved the development of degenerate consensus oligonucleotides representing putative spaced apart DNA sequences of various known molecules and the use of these oligonucleotides as primers for polymerase chain reaction (PCR) amplification of DNA replicas of intermediate gene sequences which resemble, but are not identical to, the known DNAs. The starting point for oligonucleotide primer design was the notation that the amino acids in regions surrounding cysteines which form immunoglobulin-like loops of certain CAMs are somewhat conserved. At the amino terminal side of the motif, the sequence (SEQ ID NO: 3)

G-X-X-(V or L or I)-X-(V or L or I)-X-C is found, while at the carboxy terminal side of the motif, the sequence (SEQ ID NO: 4)

N-X-G-X-Y-X-C-X-(V or A)

is typical. [See Hunkapiller et al., *Nature,* 323:15–16 (1986); Williams et al., *Ann. Rev, Immunol.,* 6:381–405 (1988); and Newman et al., supra.] In and of themselves the two amino acid motifs are much too general and do not allow the construction of degenerate sets of oligonucleotides useful as probes for unknown DNAs which might share the motif. In an attempt to solve this problem, each individual CAM sequence was split into a domain of sub files defined by the cysteine motif termini described above. Subfiles were generated for each of the seven domains of human vascular adhesion molecule (VCAM-1), the six domains of human platelet endothelial cell adhesion molecule (PECAM-1), the five domains of ICAM-1, the two domains of ICAM-2, three of the four domains of both human myeloglobin related glycoprotein and human fibroblast growth factor receptor, and the five domains of mouse neural cell adhesion molecule. All the subfiles were pooled and segregated independently from the CAM of origin using a multialignment homology computer algorithm designated "Multalin" Corpet, *Nucleic Acids Research,* 16(22):10881–10890 (1988)] providing a tree of alignment allowing the ascertainment of consensus sequences around cysteine motifs. A consensus sequence representing the amino terminal cysteine motif was determined as (SEQ ID NO: 5)

G-K-(N or S)-(L or F)-T-(L or I)-(R or E)-C, while the carboxy terminal consensus sequence was determined as (SEQ ID NO: 6)

(D or E)-(H or D)-(H or G)-(G or H)-(A or R)-N-F-S-C.

Employing human preferences for codon usage to partially eliminate degeneracy, three separate sets of oligonucleotides totalling 1152 probes were generated for use as top strand PCR primers for amplification from a putative amino terminus of the motif. The specific degenerate sequences of the three pools are set out below and respectively in SEQ ID NOS: 7, 8 and 9.

```
5'-ATTCTGCAGGCAAGAACCTGACCCTGCGCTG-3'
            A  T  C  AA CA G
                        T  T
```

-continued

```
5'-ATTCTGCAGGCAAGAGCTTCACCCTGGAGTG-3'
            A  T  T  AA C  A
                        T  T

5'-ATTCTGCAGGCAAGTCCTTCACCCTGGAGTG-3'
            A  T  T  AA C  A
                        T  T
```

Each of the primers was provided with DNA comprising a PstI restriction endonuclease recognition site (CTGCAG) to facilitate cloning of amplified products.

A total of 768 probes were designed as bottom strand primers as set out below (and in SEQ ID NOS: 10 and 11 ) for amplification from a putative carboxy terminus of the motif. Each of these primers was provided with an XbaI recognition site (TCTAGA) to facilitate cloning of amplified products.

```
5'-ATTTCTAGAGAAGTTGGCGCCGTGGTGGTC-3'
           A  A  A  C  A  A CA

5'-ATTTCTAGAGAAGTTGCGGTGGCCGTGGTC-3'
           A  A  C TA  C  A CT
```

Oligonucleotides were synthesized with an automated Applied Biosystems (Foster City, Calif.) (Model 394) DNA synthesizer using an 0.2 micromolar scale synthesis program and employing beta-cyanoethyl chemistry. Protective groups were then removed by heating at 55° C. for in excess of six hours. Oligonucleotides were then lyophilized to dryness, rehydrated in 10 mM Tris, pH 7.0, 1 mm EDTA(TE) and desalted in TE by size exclusion chromatography with G25-150 Sephadex.

EXAMPLE 2

The two sets of probes whose design and synthesis are described in Example 1 were employed in PCR amplification procedures applied to a human genomic DNA template. Briefly put, PCR-generated fragments of a size similar to that of the immunoglobulin-like loop regions of ICAM-1 and ICAM-2 were isolated, subcloned into Bluescript plasmid and screened both directly and by sequencing in arrays for hybridization with ICAM-1 and ICAM-2 DNA. Approximately 50% of the fragments were identical with ICAM-1 or ICAM-2 (except, of course, in the regions of the degenerate primer). One subclone, designated 13-3C7, was found to have an open reading frame homologous to ICAM-1 and ICAM-2 in the region of their respective second domains. It did not correspond to any known sequence present in the Genbank data base. The specific manipulations leading up to the isolation of subclone 13-3C7 were as follows.

The degenerate oligonucleotides were mixed to a final concentration of 10 ug/ml in a PCR reaction to amplify human genomic DNA obtained either from peripheral blood leukocytes or HeLa cells. The DNA amplification was performed in 2 mM $MgCl_2$, 25 mM KCl, 10 mM Tris pH 8.3 PCR buffer with 2 mM deoxynucleotides. After a 94° C. denaturation for 4 min, 35 cycles were performed with an annealing at 60° C. for 2 min, elongation at 72° C. for 4 min and denaturation at 94° C. for 1 min. A DNA band migrating at about 0.2 kb was extracted from a 6% polyacrylamide gel by electroelution, digested by XbaI and Pst 1 restriction enzymes, and ligated into the bluescript vector (Stratagene). The plasmid was electroporated into XL 1-blue strains of E.

coli (Stratagene) and colonies were selected on X-gal IPTG, carbenicillin agarose plates. Single strand templates were obtained from 6 white colonies after addition of M13K07 helper phage (Stratagene), carbenicillin, and kanamycin to a 2 ml culture of each colony. For sequence analysis, the single strand templates were then sequenced using the Sanger method both by DNA automatic sequencing (Applied Biosystems Inc.) and with a sequenase kit (UCB). Four sequences (clones 1.1, 1.3, 1.4, 1.6) were obtained which were 184–185 base pairs long and were 92–95% homologous to the second domain of ICAM-2. In addition, a 182 base pair long DNA sequence (clone 1.5) was obtained which contained a frameshift in the open reading frame of an ICAM1-like domain along with a 66 base pair DNA (clone 1.2) corresponding to a truncated immunoglobulin-like domain.

The sequence of clones 1.6, 1.5, 1.2 was used to design three oligonucleotide probes (RM16, RM15, RM12) that were used in subsequent tests to eliminate from further consideration additional colonies containing cDNAs that were highly homologous to the previous isolated clones. The sequence of probes RM16, RM15 and RM12 (SEQ ID NOS: 12, 13 and 14, respectively) is set out below.

RM16 GAGACTCTGCACTATGAGACCTTCG

RM15 CAGGTGATTCTCATGCAGAGTCCAGG

RM12 CCGACATGCTGGTAAGTGTGTCCAA

In a second round of tests, new colonies were obtained from the original PCR products that had been XbaI and Pst1 digested and from additional PCR products that had been rendered blunt-ended by treatment with the Klenow fragment of polymerase I and subcloned by blunt-end ligation. The colonies containing the vector with an insert were selected on carbenicillin L broth agarose plates containing X-gal and IPTG. Single strand templates were then synthesized in 96 wells plates by growing individual white colonies in 300 ul L broth, in which we added M13K07 phage, carbenicillin and kanamycin. Ten ul of each template were transferred with a pronging device to a nylon membrane, denatured and fixed with UV light. We transferred 10 ul of each template on three different nylon membranes for each 96 well plate. Oligonucleotides RM16, RM15, RM12 were labelled by phosphorylation using 32p gamma-ATP. The nylon membranes were pre-hybridized in 20% formamide, 5X SSC, 5X Benhardt solution and 0.5% SDS for 3 hours at 42° then hybridized overnight with the different radiolabelled oligonucleotide probes under the same condition. The membranes were then washed in 0.2 X SSC, 0.5% SDS three times for 15 min each at room temperature then washed in the same buffer at 37° for 15 min, rinsed in 2X SSC and exposed. Each template that did not hybridize with either of the three oligonucleotide probes was further sequenced using the Sanger technique by DNA automatic sequencing and by sequenase kit. Using this technique, the 170 base pair DNA sequence of clone 13-3C7 was determined.

EXAMPLE 3

The cDNA insert of subclone 13-3C7 isolated in Example 2 was used as a hybridization probe to screen four different lambda phage cDNA libraries prepared from human spleen, human placenta (two libraries) and human leukocyte cell line U937 [ATCC CRL 1593]. Briefly summarized, one hundred and twenty positive clones were picked (from among the approximately 1.6 million clones screened), subcloned, rescreened with the 13-3C7 probe, and the rescreening positives were size selected for inserts of greater than approximately 500 base pairs by analytical PCR with primers corresponding to the plasmid DNA flanking the insertion for DNAs. A 1.3 kb clone, designated clone 19C and derived from U937 cDNA, was sequenced and revealed DNA regions encoding two immunoglobulin-like domains separated by what appeared to be an intervening sequence (intron) resulting from improper or incomplete mRNA splicing prior to cDNA formation. The two regions displayed significant homology, but overall distinctness, in comparison to domains 2 and 3 of ICAM-1 and less homology to domains 1 and 2 of ICAM-2.

The specific procedures leading up to isolation of clone 19C were as follows. The four libraries were constructed in lambda GT 10 phage using cDNA obtained from the U937 cell line, from the spleen of a patient with chronic myelomonocytic leukemia and from human placenta. Exact match oligonucleotides designated 1 Hr-5' and 1Hr-3' were designed corresponding to the 5' and 3' sides of the domain-like region of subclone 13-3C7 (including bases attributable to incorporation of the original degenerate primer). The sequences of the 1 Hr-5' and 1 Hr-3' oligonucleotide primers are set out below and respectively in SEQ ID NOS: 15 and 16.

1 Hr-5' GACCATGAGGTGCCAAG

1 Hr-3' ATGGTCGTCTCTGCTGG

Using these oligonucleotides in a PCR reaction with the 13-3C7 insert template and 32p dCTP, a 148 bp long DNA probe was generated. The cDNA libraries were plated and transferred on nylon membranes. They were pre-hybridized in 40% formamide, 5X SSC, 5X Denhardt, 0.5% SDS at 42° C. for at least 15 min, then hybridized overnight with the probe in the same buffer at 42° C. The membranes were washed several times at room temperature in 2X SSC and exposed. Most of the phage plaques that hybridized with the probe were derived from the U937 cDNA library. These phages were further purified and tested by PCR (using 1 Hr-5' and 1 Hr-3' as primers) for the presence of the domain inside the cDNA clones. They were also tested by PCR to determine the length of the clones and the location of the domain within the cDNA fragment (using a combination of 13-3C7 specific primers and primers homologous to flanking gt10 vector sequences). Two clones were selected. Clone 1F was 0.7 kb long and clone 19C was 1.3 kb long. The cDNAs were digested with EcoR1 and subcloned in the Bluescript vector. In addition, the largest cDNA (clone 19C) was sonicated to obtain small pieces which were sub-cloned into Bluescript for sequencing. By homology with the ICAM-1 molecule, clone 19C cDNA contains 2 regions having homology to domains 2 and 3 of ICAM-1 respectively with an intervening sequence of unrelated DNA. Hereinafter, these DNA regions are referred to as domain 2 and domain 3 of ICAM-R.

EXAMPLE 4

The 1.3 kb (clone 19C) DNA isolated in Example 3 and having regions encoding immunoglobulin-like loops resembling domains 2 and 3 of ICAM-1 was then employed to generate a probe for the screening of additional cDNA libraries in an attempt to isolate a full length cDNA clone. Briefly, the domain 2 and 3 regions within clone 19C were each amplified by PCR using unique probes designated to match respective amino (5') and carboxy (3') terminal portions of the domains. These amplified DNAs, in turn, provided probes for screening of cDNA libraries derived from: (1) the HL60 myelomonocytic cell line; (2) lipopolysaccharide-activated human monocytes; (3) the HUT-78 T-cells (ATCC T1B161); and (4) activated peripheral blood leukocytes. The latter two libraries yielded no positives upon rescreening. Positives derived from HL60 and monocyte cDNA libraries were then screened with a probe representing of domain 2 of ICAM-1 DNA (Gen Bank, accession No. 22634 ) in order to eliminate ICAM-1 clones. A single clone derived from lambda 345 and designated pVZ-147, repeatedly tested positive for hybridization with the probe(s) based on the DNA isolated in Example 4 and negative for hybridization with the ICAM-1 DNA probe. The approximately 1.7 kb insert from clone pVZ-147 was isolated and sequenced to provide the 1781 base pair sequence set out in SEQ ID NO: 2. The deduced amino acid sequence of the polypeptide encoded by this DNA is set out in SEQ ID NO: 1. The polypeptide was designated "ICAM-R" on the basis of its structural relatedness to ICAM-1 and ICAM-2.

The specific manipulations involved in the isolation of lambda phage clone pVZ147 are as follows. All cDNA libraries were constructed in phage lambda GT10 except for the HL60 library which cloned into phage lambda 345. Oligonucleotides for use in library screening and rescreening included:

(a) probe IHr2-5' (SEQ ID NO: 17)

TTCACCCTGCGCTGCCAA;

(b) probe IHr2-3'(SEQ ID NO: 18)

AAAGGGGCTCCGTGGTCG;

(c) probe IHr 3-5'(SEQ ID NO: 19)

CCGGTTCTTGGAGGTGGAA;

(d) probe IHr 3-3'(SEQ ID NO: 20)

CATGACTGTCGCATCAGCA;

(e) probe Icam 1-5 (SEQ ID NO: 21)

GCAAGAACCTTACCCTAC; and, (f) probe Icam 1-3 (SEQ ID NO: 22)

G AAA TTGGCTCCATGGTGA.

Probes IHr 2-5' and IHr 2-3' were employed in a PCR amplification using 32PdCTP on the clone 19C template to generate a domain 2 specific probe for cDNA screening. Likewise, probes IHr 3-5' and IHr 3-3' were employed to generate a domain 3 specific probe. Finally, probes Icam 1-5 and Icam 1-3 were employed to amplify an ICAM-1 segment probe corresponding to bases 440 through 609 of the ICAM-1 cDNA sequence (Gen Bank, accession No. 22634) i.e. , the ICAM-1 second domain.

The cDNA libraries were plated, transferred on nylon membranes, hybridized with the domain 2 probe in 40% formamide, 5X SSC, 5X Denhardt, 0.5% SDS and washed as described above. All the plaques that hybridized with the domain 2 probe were derived from the monocyte and HL60 libraries. These phage plaques were purified by dilution, plating, transfer and hybridization with the domain 2 probe. To further characterize the cDNA clones, each plaque that had hybridized with the domain 2 probe was grown on an array in triplicate, transferred to a nylon membrane and hybridized under higher stringency conditions (50% formamide, 5X SSC, 5X Denhardt, 0.5% SDS) with three different probes the domain 2 probe; the domain 3 probe, and the ICAM-1 second domain probe. Six clones were found in the HL60 library and 2 clones in the monocyte library which hybridized with both domain 2 and domain 3 probes and not the ICAM-1 second domain probe. The cDNA of the 6 clones from the HL60 library were further analyzed. The phages were tested by PCR for the presence of properly spliced cDNA using oligonucleotide primers corresponding to the 5' extremity (IHr2-5') of domain 2 and to the 3' extremity (IHr3-3') of domain 3. The clones were also tested by PCR for length and location of the domains inside the clones. The cDNA plasmids were extracted and cyclized from phage lambda 345 by digestion with SfiI and self-ligation. To facilitate making single strand templates and sequencing in both orientations, each cDNA was also subcloned in bluescript SK+vector. Plasmid pVZ147 was determined to include the entire ICAM-R coding sequence in a single open reading frame.

EXAMPLE 5

A. Characterization of the ICAM-R Polypeptide

FIG. 1 graphically illustrates the sequence of the cDNA insert of the lambda phage clone pVZ 147 isolated in Example 4, above. The total of 1781 bases shown are as set out in SEQ ID NO: 2. The deduced amino acid sequence of the ICAM-R polypeptide as set out in SEQ ID NO: 1 is graphically subdivided in the Figure into the following regions:

(1) A putative signal or leader sequence is illustrated preceding the sequence of the "mature" protein and spanning amino acids designated −29 through −1. Determination of whether the translation product is actually initiated at −29 or −26 will be provided by amino acid sequencing of intracellular expression products. The designation of the first residue of the mature protein was based on generalized analogy to amino acids (and corresponding bases) for residues of secreted human proteins in the region of the junction of the mature protein and leader sequences. Confirmation of the actual initial residue of the mature protein awaits sequencing of a secreted recombinant product or, e.g., an immunopurified natural product.

(2) Within the mature protein spanning residues +1 through 518, five putative immunoglobulin-like loop regions are shown (white on black) bounded by cysteines within the five putative immunoglobulin-like domains (shown in boxes). Note that in the first domain (residues 1 through 91), cysteine residues potentially significant to loop formation are present at positions 24, 28, 67 and 71. Each of the remaining putative loops has a single relevant cysteine at each of its ends.

(3) Also within the mature protein, a putative hydrophobic "transmembrane" region is illustrated with dashes connecting residues 457 through 481 which follow the fifth immunoglobulin-like domain. A putative carboxy terminal "cytoplasmic" region constitutes residues 482 through 518.

(4) Potential N-linked glycosylation sites [characterized by the consensus sequence, Aspargine-X-(Serine or Threonine)] are indicated with an asterisk. Potential O-linked glycosylation sites occur at any serine or threonine residue.

A comparison was made between the amino acid sequence (SEQ ID NO: 1) of ICAM-R and the published 537 residue amino acid sequence of ICAM-1 (GenBank accession No. 22634; cf, FIG. 8 of European Patent Application 0 289 949 published Nov. 11, 1988). This comparison revealed 249 matches within the aligned 537 residues, indicating an overall amino acid homology of 46% between the two polypeptides. The highest percentage of matches was noted to be present in domains 2 and 3 of ICAM-1 and putative domains 2 and 3 of ICAM-R. Likewise the alignment of SEQ ID NO: 1 with the published 295 residues of the amino acid sequence of ICAM-2 (GenBank accession No. 22635; cf, FIG. 2 of European Patent Application 0 387 668 published Sep. 19, 1990) revealed 78 matches among the 282 aligned residues, for a 27% overall homology of amino acids.

B. Characterization of ICAM-R DNA

A comparative alignment of the ICAM-R DNA sequence (SEQ ID NO: 2) was made with the published DNA sequences of ICAM-1 and ICAM-2, supra. A total of 677 matches were noted among the 1623 aligned bases of ICAM-R and ICAM-1 providing an overall homology of 41%. A 42% homology (484 matches) between the aligned 1136 bases of ICAM-R and ICAM-2 DNAs was noted.

Reference points in the FIG. 1 DNA having "historical" significance to the isolation of the ICAM-R gene include the following:

(a) bases 420 through 567 correspond to the subclone 13-3C7 isolated in Example 2;

(b) bases 373 through 663 correspond to the immunoglobulin-like domain 2 localized in clone 19C of Example 3 (with bases 418 through 435 and 561 through 578, respectively corresponding to probes IHr2-5' and IHr2-3' employed for PCR amplification of domain 2 to provide one of the oligonucleotide probes for use in Example 4); and (c) bases 664 through 957 correspond to the immunoglobulin-like domain 3 localized on clone 19C of Example 3 (with bases 699 through 717 and 800 through 819, respectively corresponding to probes IHr3-5' and IHr3-3' employed for PCR amplification of domain 3 to provide another oligonucleotide probe for use in Example 4.

EXAMPLE 6

Expression of ICAM-R in COS-7 monkey kidney cells and LTK mouse cells is effected as follows. The full length ICAM-R cDNA insert of pVZ-147 and a small portion of the phagmid vector 3' to the cDNA insert was excised using NotI and XbaI and ligated into commercial plasmid pCDNA1-neo (Invitrogen Inc.) cut with NotI and XbaI. The resulting plasmid, designated pCDNA1-neo-ICAM-R, was transfected into COS-7 cells and into mouse L cells by lipofection using the cationic lipid, DOTAP (Boehringer-Mannheim) in an attempt to secure both transient and stable expression of ICAM-R RNA and protein.

The foregoing illustrative examples relate to presently preferred embodiments of the invention and numerous modifications and variations thereof will be expected to occur to those skilled in the art.

Clearly, polynucleotides (DNA, RNA) encoding ICAM-R are useful not only in securing expression of ICAM-R and variant polypeptides; they may readily be employed to identify cells (especially cells involved in inflammatory processes) which express ICAM-R in a normal or activated state. Typical detection assays involving ICAM-R DNA include Northern blot hybridization, RNAse protection, and in situ hybridization cytological assays wherein the DNA or RNA (in suitably labelled, detectable form) hybridizes to RNA in the sample. Preliminary in situ screening of human tonsil tissue with radiolabelled ICAM-R specific RNA probes has revealed that significant numbers of cells contain ICAM-R-specifying RNA. ICAM-R encoding DNA (especially DNA encoding the first, fourth and fifth domains which have less homology to DNAs for ICAM-1 and ICAM-2 than the DNAs encoding domains 2 and 3, is expected to be useful in isolating genomic DNA encoding ICAM-R including genomic DNA specifying endogenous expression control DNA sequences for ICAM-R DNA. As previously noted, knowledge of polynucleotide sequences encoding ICAM-R and/or controlling expression of ICAM-R makes available a variety of antisense polynucleotides useful in regulating expression of ICAM-R.

The present invention makes available the production of ICAM-R polypeptides and variants thereof, especially including water soluble fragments thereof such as fragments comprising one or more of the five immunoglobulin-like domains of ICAM-R in glycosylated, non-glycosylated, or de-glycosylated forms. Pharmaceutical compositions including the protein products of the invention have therapeutic potential in the treatment of inflammatory disease processes, e.g., as competitive inhibitors of ligand/receptor binding reactions involving ICAM-R. Such therapeutic potential is especially projected for "immunoadhesin" type recombinant hybrid fusion proteins containing, at their amino terminal, one or more domains of ICAM-R and, at their carboxy terminal, at least one constant domain of an immunoglobulin. Such hybrids are likely to be available in the form of homodimers wherein the Ig portion provides for longer serum half life and the ICAM-R portion has greater affinity for the ICAM-R binding partner than ICAM-R R itself.

Antibody substances and binding proteins, especially monospecific antibodies including monoclonal and polyclonal antibodies are made readily available by the present invention through the use of immunogens comprising recombinant host cells and cells naturally expressing ICAM-R or polypeptide products of the invention. Such antibodies and other ICAM-R specific binding proteins can be employed for immunopurification of ICAM-R and variants and in pharmaceutical compositions for therapies premised on blocking the ligand/receptor binding of ICAM-R and soluble fragments thereof. Antibodies specific for distinct regions of ICAM-R may be employed in ELISA systems involving immunological "sandwiches" for monitoring inflammatory processes characterized by increases in amounts of soluble ICAM-R polypeptides in body fluids such as serum.

Thus only such limitations as appear in the appended claims should be placed upon the scope of the present invention.

What is claimed is:

1. A purified and isolated ICAM-R polynucleotide having the sequence set out in SEQ ID NO: 2.

2. A purified and isolated polynucleotide encoding an ICAM-R polypeptide having the sequence set out in SEQ ID NO: 1.

3. A purified and isolated polynucleotide encoding an ICAM-R polypeptide having amino acids 1 to 518 of SEQ ID NO: 1.

4. A purified and isolated polynucleotide encoding an ICAM-R polypeptide having amino acids 1 to 90 of SEQ ID NO: 1.

5. A purified and isolated polynucleotide encoding an ICAM-R polypeptide having amino acids 91 to 187 of SEQ ID NO: 1.

6. A purified and isolated polynucleotide encoding an ICAM-R polypeptide having amino acids 188 to 285 of SEQ ID NO: 1.

7. A purified and isolated polynucleotide encoding an ICAM-R polypeptide having amino acids 286 to 387 of SEQ ID NO: 1.

8. A purified and isolated polynucleotide encoding an ICAM-R polypeptide having amino acids 388 to 456 of SEQ ID NO: 1.

9. A purified and isolated polynucleotide encoding an ICAM-R polypeptide having amino acids 24 to 71 of SEQ ID NO: 1.

10. A purified and isolated polynucleotide encoding an ICAM-R polypeptide having amino acids 110 to 160 of SEQ ID NO: 1.

11. A purified and isolated polynucleotide encoding an ICAM-R polypeptide having amino acids 212 to 265 of SEQ ID NO: 1.

12. A purified and isolated polynucleotide encoding an ICAM-R polypeptide having amino acids 307 to 346 of SEQ ID NO: 1.

13. A purified and isolated polynucleotide encoding an ICAM-R polypeptide having amino acids 394 to 433 of SEQ ID NO: 1.

14. A purified and isolated polynucleotide encoding an ICAM-R polypeptide having amino acids 457 to 518 of SEQ ID NO: 1.

15. A purified and isolated polynucleotide encoding an ICAM-R polypeptide having amino acids 482 to 518 of SEQ ID NO: 1.

16. A purified and isolated polynucleotide encoding an ICAM-R polypeptide having amino acids 1 to 456 of SEQ. ID NO:1.

17. A purified and isolated polynucleotide encoding an ICAM-R polypeptide having amino acids 1-481 of SEQ. ID No:1.

18. A full length, purified and isolated ICAM-R polynucleotide selected from the group consisting of:

(a) a polynucleotide consisting of the protein coding portion of the sequence set forth in SEQ. ID NO:2;

(b) a polynucleotide which hybridizes at 42° C. in 50% formamide and 5X SSC to the antisense stand of the polynucleotide of (a).

19. A polynucleotide encoding a hybrid fusion polypeptide, said hybrid fusion protein comprising, at its amino terminus, an ICAM-R polypeptide comprising the amino acids 1 to 518 of the sequence set out in SEQ ID NO: 1 and, at its carboxy terminus, at least one constant domain of an immunoglobulin heavy chain.

20. An antisense polynucleotide specific for the ICAM-R polynucleotide having the sequence set out in SEQ ID NO: 1.

21. A DNA vector comprising a polynucleotide sequence according to claims 1, 2, 3, 4, 5, 6, 7, 8, 9, 10, 11, 12, 13, 14, 15, 16, 17 18, or 19.

22. The DNA vector of claim 21 which is plasmid pcDNA-1-neo-ICAM-R.

23. The DNA vector of claim 22 wherein said polynucleotide sequence is operatively linked to an expression control DNA sequence.

24. A host cell stably transformed or transfected with a DNA according to claim 1, 2, 3, 4, 5, 6, 7, 8, 9, 10, 11, 12, 13, 14, 15, 16, 17, 18, or 19.

25. A method for producing ICAM-R polypeptide comprising the steps of growing a host cell according to claim 24 in a suitable nutrient medium and isolating ICAM-R polypeptide from said cell or the medium of its growth.

* * * * *

UNITED STATES PATENT AND TRADEMARK OFFICE

CERTIFICATE OF CORRECTION

PATENT NO. : 5,525,487

DATED : June 11, 1996

INVENTORS : Gallatin *et al.*

It is certified that error appears in the above-identified patent and that said Letters Patent is hereby corrected as shown below:

column 1, line 44 replace "Supra" with --supra--;

column 1, line 59 replace "Nov." with --November--;

column 1, line 62 replace "Jul." with --July--;

column 2, line 45 replace "inter alia" with --inter alia--;

column 3, line 29 replace "infra" with --infra--;

column 5, line 24 replace "supra" with --supra--;

column 6, line 11 replace "PstI" with --PstI--;

column 6, line 16 replace "XbaI with --XbaI--;

column 6, line 65 replace "XbaI with --XbaI--;

column 6, line 65 replace "Pst 1" with --PstI--;

column 7, line 32 replace "XbaI" with --XbaI--;

column 7, line 32 replace "Pst1" with --PstI--;

column 8, line 49 replace "0.7 kb" with --0.7kb--;

UNITED STATES PATENT AND TRADEMARK OFFICE

CERTIFICATE OF CORRECTION

PATENT NO. : 5,525,487

DATED : June 11, 1996

INVENTORS : Gallatin *et al.*

It is certified that error appears in the above-identified patent and that said Letters Patent is hereby corrected as shown below:

column 9, line 46 replace "CATGACTGTCGCATCAGCA" with --CATGACTGTCGCATTCAGCA--;

column 9, line 58 replace "32PdCTP" with --$^{32}$PdCTP--;

column 10, line 23 replace "SfiI" with --SfiI--;

column 11, line 8 replace "cf" with --cf--;

column 11, line 9 replace "Nov." with --November--;

column 11, line 17 replace "cf" with --cf--;

column 11, line 26 replace "supra" with --supra-;

column 11, line 54 replace "NotI" with --NotI--;

column 11, line 55 replace "XbaI" with --XbaI--;

column 11, line 56 replace "NotI" with --NotI--;

column 11, line 56 replace "XbaI" with --XbaI--;

column 12, line 9 replace "in situ" with --in situ--;

UNITED STATES PATENT AND TRADEMARK OFFICE

CERTIFICATE OF CORRECTION

PATENT NO. : 5,525,487

DATED : June 11, 1996

INVENTORS : Gallatin *et al.*

It is certified that error appears in the above-identified patent and that said Letters Patent is hereby corrected as shown below:

column 12, line 11 replace "in situ" with --in situ--;

column 12, line 44 replace "ICAM-R R" with --ICAM-R--;

Signed and Sealed this

Sixth Day of January, 1998

Attest:

BRUCE LEHMAN

*Attesting Officer*

*Commissioner of Patents and Trademarks*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 547 amino acids
( B ) TYPE: amino acid
( D ) TOPOLOGY: linear ( i i ) MOLECULE TYPE: protein ( i x ) FEATURE:
( A ) NAME/KEY: Protein
( B ) LOCATION: 30..547

( x i ) SEQUENCE DESCRIPTION: SEQ ID NO:1:

| | | | | | | | | | | | | | | | |
|---|---|---|---|---|---|---|---|---|---|---|---|---|---|---|---|
| Met | Ala | Thr | Met | Val | Pro | Ser | Val | Leu | Trp | Pro | Arg | Ala | Cys | Trp | Thr |
| | | | | -25 | | | | | -20 | | | | | -15 | |
| Leu | Leu | Val | Cys | Cys | Leu | Leu | Thr | Pro | Gly | Val | Gln | Gly | Gln | Glu | Phe |
| | | | -10 | | | | | -5 | | | | | 1 | | |
| Leu | Leu | Arg | Val | Glu | Pro | Gln | Asn | Pro | Val | Leu | Ser | Ala | Gly | Gly | Ser |
| | 5 | | | | | 10 | | | | | 15 | | | | |
| Leu | Phe | Val | Asn | Cys | Ser | Thr | Asp | Cys | Pro | Ser | Ser | Glu | Lys | Ile | Ala |
| 20 | | | | | 25 | | | | | 30 | | | | | 35 |
| Leu | Glu | Thr | Ser | Leu | Ser | Lys | Glu | Leu | Val | Ala | Ser | Gly | Met | Gly | Trp |
| | | | | 40 | | | | | 45 | | | | | 50 | |
| Ala | Ala | Phe | Asn | Leu | Ser | Asn | Val | Thr | Gly | Asn | Ser | Arg | Ile | Leu | Cys |
| | | | 55 | | | | | 60 | | | | | 65 | | |
| Ser | Val | Tyr | Cys | Asn | Gly | Ser | Gln | Ile | Thr | Gly | Ser | Ser | Asn | Ile | Thr |
| | | 70 | | | | | 75 | | | | | 80 | | | |
| Val | Tyr | Gly | Leu | Pro | Glu | Arg | Val | Glu | Leu | Ala | Pro | Leu | Pro | Pro | Trp |
| | 85 | | | | | 90 | | | | | 95 | | | | |
| Gln | Pro | Val | Gly | Gln | Asn | Phe | Thr | Leu | Arg | Cys | Gln | Val | Glu | Gly | Gly |
| 100 | | | | | 105 | | | | | 110 | | | | | 115 |
| Ser | Pro | Arg | Thr | Ser | Leu | Thr | Val | Val | Leu | Leu | Arg | Trp | Glu | Glu | Glu |
| | | | | 120 | | | | | 125 | | | | | 130 | |
| Leu | Ser | Arg | Gln | Pro | Ala | Val | Glu | Glu | Pro | Ala | Glu | Val | Thr | Ala | Thr |
| | | | 135 | | | | | 140 | | | | | 145 | | |
| Val | Leu | Ala | Ser | Arg | Asp | Asp | His | Gly | Ala | Pro | Phe | Ser | Cys | Arg | Thr |
| | | 150 | | | | | 155 | | | | | 160 | | | |
| Glu | Leu | Asp | Met | Gln | Pro | Gln | Gly | Leu | Gly | Leu | Phe | Val | Asn | Thr | Ser |
| | 165 | | | | | 170 | | | | | 175 | | | | |
| Ala | Pro | Arg | Gln | Leu | Arg | Thr | Phe | Val | Leu | Pro | Val | Thr | Pro | Pro | Arg |
| 180 | | | | | 185 | | | | | 190 | | | | | 195 |
| Leu | Val | Ala | Pro | Arg | Phe | Leu | Glu | Val | Glu | Thr | Ser | Trp | Pro | Val | Asp |
| | | | | 200 | | | | | 205 | | | | | 210 | |
| Cys | Thr | Leu | Asp | Gly | Leu | Phe | Pro | Ala | Ser | Glu | Ala | Gln | Val | Tyr | Leu |
| | | | 215 | | | | | 220 | | | | | 225 | | |
| Ala | Leu | Gly | Asp | Gln | Met | Leu | Asn | Ala | Thr | Val | Met | Asn | His | Gly | Asp |
| | | 230 | | | | | 235 | | | | | 240 | | | |
| Thr | Leu | Thr | Ala | Thr | Ala | Thr | Ala | Thr | Ala | Arg | Ala | Asp | Gln | Glu | Gly |
| | 245 | | | | | 250 | | | | | 255 | | | | |
| Ala | Arg | Glu | Ile | Val | Cys | Asn | Val | Thr | Leu | Gly | Gly | Glu | Arg | Arg | Glu |
| 260 | | | | | 265 | | | | | 270 | | | | | 275 |

-continued

Ala Arg Glu Asn Leu Thr Val Phe Ser Phe Leu Gly Pro Ile Val Asn
280 285 290

Leu Ser Glu Pro Thr Ala His Glu Gly Ser Thr Val Thr Val Ser Cys
295 300 305

Met Ala Gly Ala Arg Val Gln Val Thr Leu Asp Gly Val Pro Ala Ala
310 315 320

Ala Pro Gly Gln Thr Ala Gln Leu Gln Leu Asn Ala Thr Glu Ser Asp
325 330 335

Asp Gly Arg Ser Phe Phe Cys Ser Ala Thr Leu Glu Val Asp Gly Glu
340 345 350 355

Phe Leu His Arg Asn Ser Ser Val Gln Leu Arg Val Leu Tyr Gly Pro
360 365 370

Lys Ile Asp Arg Ala Thr Cys Pro Gln His Leu Lys Trp Lys Asp Lys
375 380 385

Thr Arg His Val Leu Gln Cys Gln Ala Arg Gly Asn Pro Tyr Pro Glu
390 395 400

Leu Arg Cys Leu Lys Glu Gly Ser Ser Arg Glu Val Pro Val Gly Ile
405 410 415

Pro Phe Phe Val Asn Val Thr His Asn Gly Thr Tyr Gln Cys Gln Ala
420 425 430 435

Ser Ser Ser Arg Gly Lys Tyr Thr Leu Val Val Val Met Asp Ile Glu
440 445 450

Ala Phe Ser Ser His Phe Val Pro Val Phe Val Ala Val Leu Leu Thr
455 460 465

Leu Gly Val Val Thr Ile Val Leu Ala Leu Met Tyr Val Phe Arg Glu
470 475 480

His Gln Arg Ser Gly Ser Tyr His Val Arg Glu Glu Ser Thr Tyr Leu
485 490 495

Pro Leu Thr Ser Met Gln Pro Thr Glu Ala Met Gly Glu Glu Pro Ser
500 505 510 515

Arg Ala Glu ( 2 ) INFORMATION FOR SEQ ID NO:2:

( i ) SEQUENCE CHARACTERISTICS:
( A ) LENGTH: 1781 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:2:

CAGCTCTCTG TCAGAATGGC CACCATGGTA CCATCCGTGT TGTGGCCCAG GGCCTGCTGG 60

ACTCTGCTGG TCTGCTGTCT GCTGACCCCA GGTGTCCAGG GGCAGGAGTT CCTTTTGCGG 120

GTGGAGCCCC AGAACCCTGT GCTCTCTGCT GGAGGGTCCC TGTTTGTGAA CTGCAGTACT 180

GATTGTCCCA GCTCTGAGAA AATCGCCTTG GAGACGTCCC TATCAAAGGA GCTGGTGGCC 240

AGTGGCATGG GCTGGGCAGC CTTCAATCTC AGCAACGTGA CTGGCAACAG TCGGATCCTC 300

TGCTCAGTGT ACTGCAATGG CTCCCAGATA ACAGGCTCCT CTAACATCAC CGTGTACGGG 360

CTCCCGGAGC GTGTGGAGCT GGCACCCCTG CCTCCTTGGC AGCCGGTGGG CCAGAACTTC 420

ACCCTGCGCT GCCAAGTGGA GGGTGGGTCG CCCCGGACCA GCCTCACGGT GGTGCTGCTT 480

CGCTGGGAGG AGGAGCTGAG CCGGCAGCCC GCAGTGGAGG AGCCAGCGGA GGTCACTGCC 540

ACTGTGCTGG CCAGCAGAGA CGACCACGGA GCCCCTTTCT CATGCCGCAC AGAACTGGAC 600

-continued

| | | | | | | |
|---|---|---|---|---|---|---|
| ATGCAGCCCC | AGGGGCTGGG | ACTGTTCGTG | AACACCTCAG | CCCCCCGCCA | GCTCCGAACC | 660 |
| TTTGTCCTGC | CCGTGACCCC | CCCGCGCCTC | GTGGCCCCCC | GGTTCTTGGA | GGTGGAAACG | 720 |
| TCGTGGCCGG | TGGACTGCAC | CCTAGACGGG | CTTTTTCCAG | CCTCAGAGGC | CCAGGTCTAC | 780 |
| CTGGCGCTGG | GGGACCAGAT | GCTGAATGCG | ACAGTCATGA | ACCACGGGGA | CACGCTAACG | 840 |
| GCCACAGCCA | CAGCCACGGC | GCGCGCGGAT | CAGGAGGGTG | CCCGGGAGAT | CGTCTGCAAC | 900 |
| GTGACCCTAG | GGGGCGAGAG | ACGGGAGGCC | CGGGAGAACT | TGACGGTCTT | TAGCTTCCTA | 960 |
| GGACCCATTG | TGAACCTCAG | CGAGCCCACC | GCCCATGAGG | GGTCCACAGT | GACCGTGAGT | 1020 |
| TGCATGGCTG | GGGCTCGAGT | CCAGGTCACG | CTGGACGGAG | TTCCGGCCGC | GGCCCCGGGG | 1080 |
| CAGACAGCTC | AACTTCAGCT | AAATGCTACC | GAGAGTGACG | ACGGACGCAG | CTTCTTCTGC | 1140 |
| AGTGCCACTC | TCGAGGTGGA | CGGCGAGTTC | TTGCACAGGA | ACAGTAGCGT | CCAGCTGCGA | 1200 |
| GTCCTGTATG | GTCCCAAAAT | TGACCGAGCC | ACATGCCCCC | AGCACTTGAA | ATGGAAAGAT | 1260 |
| AAAACGAGAC | ACGTCCTGCA | GTGCCAAGCC | AGGGGCAACC | CGTACCCCGA | GCTGCGGTGT | 1320 |
| TTGAAGGAAG | GCTCCAGCCG | GGAGGTGCCG | GTGGGGATCC | CGTTCTTCGT | CAACGTAACA | 1380 |
| CATAATGGTA | CTTATCAGTG | CCAAGCGTCC | AGCTCACGAG | GCAAATACAC | CCTGGTCGTG | 1440 |
| GTGATGGACA | TTGAGGCTGG | GAGCTCCCAC | TTTGTCCCCG | TCTTCGTGGC | GGTGTTACTG | 1500 |
| ACCCTGGGCG | TGGTGACTAT | CGTACTGGCC | TTAATGTACG | TCTTCAGGGA | GCACCAACGG | 1560 |
| AGCGGCAGTT | ACCATGTTAG | GGAGGAGAGC | ACCTATCTGC | CCCTCACGTC | TATGCAGCCG | 1620 |
| ACAGAAGCAA | TGGGGGAAGA | ACCGTCCAGA | GCTGAGTGAC | GCTGGGATCC | GGGATCAAAG | 1680 |
| TTGGCGGGGG | CTTGGCTGTG | CCCTCAGATT | CCGCACCAAT | AAAGCCTTCA | AACTCCCAAA | 1740 |
| AAAAAAAAAA | AAAAAAAAAA | AAAAAAAAAA | AAAAAAAAAA | A | | 1781 |

( 2 ) INFORMATION FOR SEQ ID NO:3:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 4
( D ) OTHER INFORMATION: /note="The amino acid at this position can be a valine, a leucine or an isoleucine."

( i x ) FEATURE:
( A ) NAME/KEY: Modified-site
( B ) LOCATION: 6
( D ) OTHER INFORMATION: /note="The amino acid at this position can be a valine, a leucine or an isoleucine."

( x i ) SEQUENCE DESCRIPTION: SEQ ID NO:3:

Gly Xaa Xaa Xaa Xaa Xaa Xaa Cys
1 5

( 2 ) INFORMATION FOR SEQ ID NO:4:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( i x ) FEATURE:

( A ) NAME/KEY: Modified-site
( B ) LOCATION: 9
( D ) OTHER INFORMATION: /note="The amino acid at this position can be a valine or an alanine."

( x i ) SEQUENCE DESCRIPTION: SEQ ID NO:4:

Asp Xaa Gly Xaa Tyr Xaa Cys Xaa Xaa
1 5

( 2 ) INFORMATION FOR SEQ ID NO:5:

( i ) SEQUENCE CHARACTERISTICS:
( A ) LENGTH: 8 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 3
( D ) OTHER INFORMATION: /note="The amino acid at this position can be an asparagine or a serine."

( i x ) FEATURE:
( A ) NAME/KEY: Modified-site
( B ) LOCATION: 4
( D ) OTHER INFORMATION: /note="The amino acid at this position can be a lysine or a phenylalanine."

( i x ) FEATURE:
( A ) NAME/KEY: Modified-site
( B ) LOCATION: 6
( D ) OTHER INFORMATION: /note="The amino acid at this position can be an lysine or an isoleucine."

( i x ) FEATURE:
( A ) NAME/KEY: Modified-site
( B ) LOCATION: 7
( D ) OTHER INFORMATION: /note="The amino acid at this position can be an arginine or a glutamic acid."

( x i ) SEQUENCE DESCRIPTION: SEQ ID NO:5:

Gly Lys Xaa Xaa Thr Xaa Xaa Cys
1 5

( 2 ) INFORMATION FOR SEQ ID NO:6:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="The amino acid at this position can be a aspartic acid or a glutamic acid."

( i x ) FEATURE:
( A ) NAME/KEY: Modified-site
( B ) LOCATION: 2
( D ) OTHER INFORMATION: /note="The amino acid at this position can be a histidine or an aspartic acid."

( i x ) FEATURE:
( A ) NAME/KEY: Modified-site
( B ) LOCATION: 3
( D ) OTHER INFORMATION: /note="The amino acid at this position can be a histidine or a glycine."

( i x ) FEATURE:
( A ) NAME/KEY: Modified-site

-continued ( B ) LOCATION: 4
( D ) OTHER INFORMATION: /note="The amino acid at this position can be a glycine or a histidine."

( i x ) FEATURE:
( A ) NAME/KEY: Modified-site
( B ) LOCATION: 5
( D ) OTHER INFORMATION: /note="The amino acid at this position can be an alanine or an arginine."

( x i ) SEQUENCE DESCRIPTION: SEQ ID NO:6:

Xaa Xaa Xaa Xaa Xaa Asn Phe Ser Cys
1 5

( 2 ) INFORMATION FOR SEQ ID NO:7:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:7:

ATTCTGCAGG CAARAAYCTS ACHMTBMGST G 31

( 2 ) INFORMATION FOR SEQ ID NO:8:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:8:

ATTCTGCAGG CAARAGYTTY ACHMTBGART G 31

( 2 ) INFORMATION FOR SEQ ID NO:9:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:9:

ATTCTGCAGG CAARTCYTTY ACHMTBGART G 31

( 2 ) INFORMATION FOR SEQ ID NO:10:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:10:

ATTTCTAGAR AARTTRGCSC CRTGRTSRTC 30

( 2 ) INFORMATION FOR SEQ ID NO:11:

( i ) SEQUENCE CHARACTERISTICS:
( A ) LENGTH: 30 base pairs ( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:11:

ATTTCTAGAR AARTTSCKRT GSCCRTSKTC 30

( 2 ) INFORMATION FOR SEQ ID NO:12:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:12:

GAGACTCTGC ACTATGAGAC CTTCG 25

( 2 ) INFORMATION FOR SEQ ID NO:13:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:13:

CAGGTGATTC TCATGCAGAG TCCAGG 26

( 2 ) INFORMATION FOR SEQ ID NO:14:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:14:

CCGACATGCT GGTAAGTGTG TCCAA 25

( 2 ) INFORMATION FOR SEQ ID NO:15:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:15:

GACCATGAGG TGCCAAG 17

( 2 ) INFORMATION FOR SEQ ID NO:16:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA -continued ( x i ) SEQUENCE DESCRIPTION: SEQ ID NO:16:

ATGGTCGTCT CTGCTGG 17

( 2 ) INFORMATION FOR SEQ ID NO:17:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:17:

TTCACCCTGC GCTGCCAA 18

( 2 ) INFORMATION FOR SEQ ID NO:18:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:18:

AAAGGGGCTC CGTGGTCG 18

( 2 ) INFORMATION FOR SEQ ID NO:19:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:19:

CCGGTTCTTG GAGGTGGAA 19

( 2 ) INFORMATION FOR SEQ ID NO:20:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:20:

CATGACTGTC GCATTCAGCA 20

( 2 ) INFORMATION FOR SEQ ID NO:21:

( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:21:

GCAAGAACCT TACCCTAC 18

-continued ( 2 ) INFORMATION FOR SEQ ID NO:22:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:22:

GAAATTGGCT CCATGGTGA 19